(12) United States Patent
England et al.

(10) Patent No.: US 6,769,612 B1
(45) Date of Patent: Aug. 3, 2004

(54) DETERMINING PROPERTIES OF MAGNETIC ELEMENTS

(75) Inventors: James Mark Carson England, Cambridge (GB); Andrew Nicholas Dames, Cambridge (GB)

(73) Assignee: BTG International Limited, London (GB)

(*) Notice: Subject to any disclaimer, the term of this patent is extended or adjusted under 35 U.S.C. 154(b) by 0 days.

(21) Appl. No.: 10/049,420

(22) PCT Filed: Aug. 11, 2000

(86) PCT No.: PCT/GB00/03092

§ 371 (c)(1),
(2), (4) Date: May 21, 2002

(87) PCT Pub. No.: WO01/13321

PCT Pub. Date: Feb. 22, 2001

(30) Foreign Application Priority Data

Aug. 12, 1999 (GB) .............................. 9919100

(51) Int. Cl.[7] .............................. G06F 17/60
(52) U.S. Cl. .................. 235/385; 235/449; 235/493; 235/487; 340/551; 340/552
(58) Field of Search ............................. 235/385, 449, 235/493, 487; 360/1, 2; 340/551, 552

(56) References Cited

U.S. PATENT DOCUMENTS

| | | | | |
|---|---|---|---|---|
| 4,635,227 A | * | 1/1987 | Normann | 365/133 |
| 5,175,419 A | * | 12/1992 | Yamashita | 235/449 |
| 5,204,526 A | | 4/1993 | Yamashita et al. | 235/493 |
| 6,040,773 A | * | 3/2000 | Vega et al. | 340/572.1 |
| 6,170,748 B1 | * | 1/2001 | Hash et al. | 235/451 |
| 6,371,379 B1 | * | 4/2002 | Dames et al. | 235/493 |
| 6,373,388 B1 | * | 4/2002 | Dames | 340/572.2 |
| 6,556,139 B2 | * | 4/2003 | Manov et al. | 340/572.6 |

FOREIGN PATENT DOCUMENTS

| WO | 99 09436 A | 2/1999 |
|---|---|---|
| WO | 99 35610 A | 7/1999 |

* cited by examiner

Primary Examiner—Michael G. Lee
Assistant Examiner—Steven S. Paik
(74) Attorney, Agent, or Firm—Nixon & Vanderhye P.C.

(57) ABSTRACT

A method of determining differing characteristics of magnetic dipole elements such as orientation, coercivity, bias and response amplitude and a tag reader for reading magnetic tags containing such elements. The elements are scanned by a rotating magnetic field and two sets of transition data are determined. The transition data sets are associated with respective elements and analyzed to determine mean field values resolved along the element vectors. These field values are used to determine properties of the elements, such as coercivity.

28 Claims, 19 Drawing Sheets ical application PCT/GB00/03092 filed 11 Aug. 2000, which designated the U.S.

DETERMINING PROPERTIES OF MAGNETIC ELEMENTS

This application is the U.S. national phase of international application PCT/GB00/03092 filed 11 Aug. 2000, which designated the U.S.

FIELD OF THE INVENTION

This invention relates to magnetic elements, particularly but not exclusively to methods of distinguishing between magnetic elements and methods and apparats for reading magnetic data tags which include one or more magnetic elements, each of which can differ in coercivity, saturated dipole moment (i.e. response amplitude), orientation and bias field.

BACKGROUND

Co-pending PCT publication number WO99/35610 describes tags and reader systems primarily intended for tags fabricated from magnetic material of low coercivity, with elements at different orientations, in which data is recorded primarily by means of the orientation of the elements with respect to each other. The described system assumes that the coercivities of the tag elements are all the same, and arc very small compared to the interrogation field.

SUMMARY OF THE INVENTION

According to the invention, there is provided a method of reading a magnetic tag having at least one magnetic element, comprising interrogating the tag with a scanning magnetic field, determining transition data associated with changes in the magnetisation state of the at least one magnetic element, associating the transition data with one or more respective elements; and for each element, determining the element direction which corresponds to the transition data for that element.

Preferably, the element direction is determined by selecting the direction that minimises the scatter of the transition field vectors resolved along the direction of the element.

The transition data for each element can be grouped into two sets, which can be referred to as forward and reverse transitions. All those in the forward transition group have a positive component of the field vector dH/dt along the element vector, and all those in the reverse group have a negative component of dH/dt along the element vector. Mean field values, resolved along the element vector, can be calculated. The coercivity of the element is then calculated as half the difference between the forward and reverse mean values, and the bias field along the element is calculated as the sum of the forward and reverse mean value According to the invention, there is further provided a method of distinguishing between a plurality of magnetic elements, comprising the steps of applying a scanning magnetic field to the elements, determining the direction of each of the elements, for each of the elements, determining the components of the field in the direction of the element at which the element switches magnetisation states; and from said components, determining, for each of the elements, respective characteristics of the element.

The invention further provides a method of determining, for a magnetic element, any one or more of a plurality of characteristics comprising the coercivity of the element, the local magnetic field bias resolved in the direction of the element and the orientation of the element, comprising the steps of applying a varying magnetic field to the element, determining the direction of the element, determining tie components of the field in the direction of the element at which the element switches magnetisation states; and from said components, determining the one or more characteristics of the element.

According to the invention, there is also provided a magnetic tag reader for reading a magnetic tag having at least one magnetic element, comprising means for interrogating the tag with a scanning magnetic field, means for determining transition data associated with changes in the magnetisation state of the at least one magnetic element, means for associating the transition data with one or more respective elements; and means for determining, for each element, the element direction which corresponds to the transition data for that element

BRIEF DESCRIPTION OF THE DRAWINGS

Embodiments of the invention will now be described, by way of example, with reference to the accompanying drawings, in which:

FIG. 20 illustrates the same 3D scatter plot as FIG. 19, tilted such that the transition planes are edge-on;

DETAILED DESCRIPTION

Figure 1:
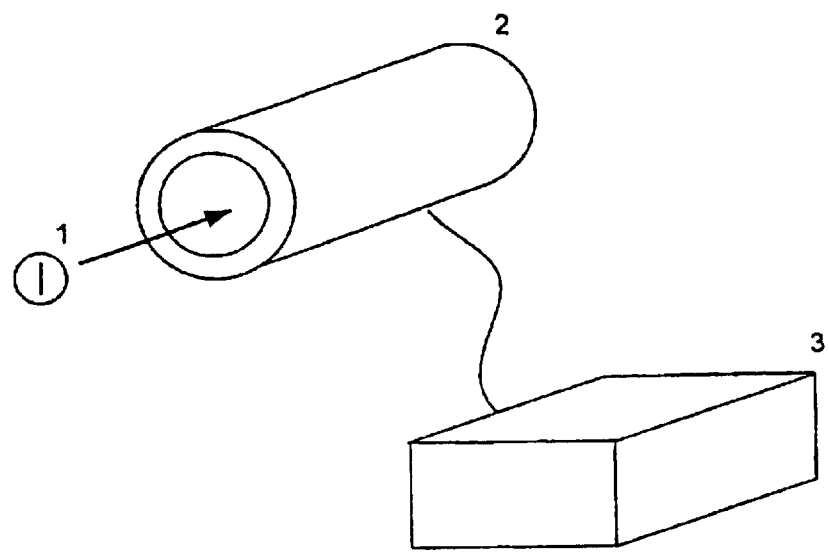
FIG. 1 is a schematic diagram of a magnetic data tag reading system.
Figure 2:
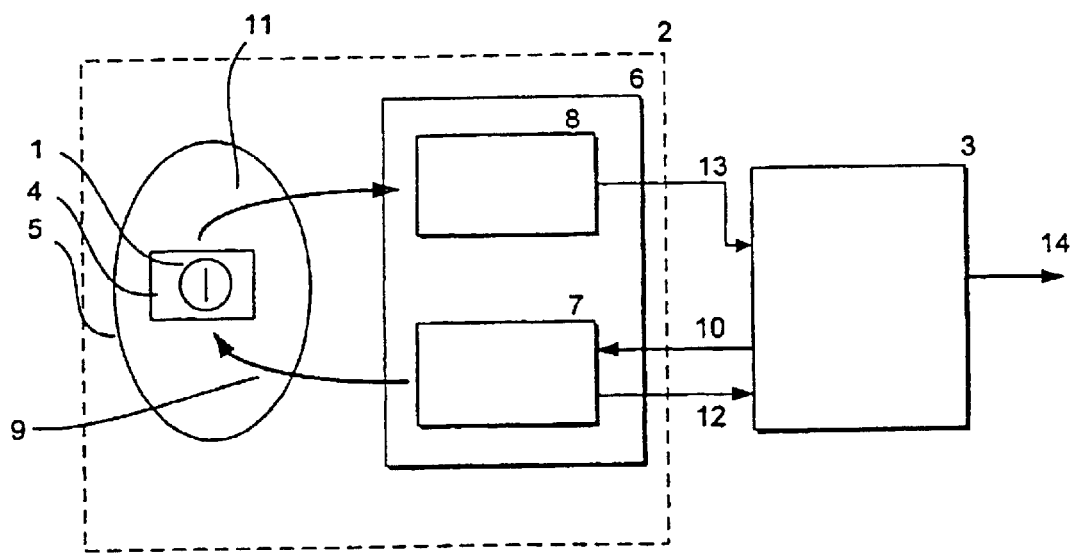
FIG. 2 is a schematic diagram showing the components of the magnetic data tag reading system of FIG. 1 in more detail.

Referring to FIG. 1, a magnetic tag reading system comprises a magnetic data tag 1, an interrogation unit 2 and a signal processor/controller 3. Magnetic tags 1 to be used with a magnetic tag reader according to the invention can record information by means of elements of differing coercivities, local bias fields and response amplitudes, as well as orientation This includes tags described in PCT publication number WO99/35610, as well as tags described in, for example, U.S. 5,204,526, U.S. 5,729,201 and WO98/26312. In general terms, magnetic tags 1 comprise magnetic elements which typically switch magnetisation state, for example magnetisation direction, at given values of applied field depending on element properties, for example coercivity. These elements include, for example, thin film elements, bistable elements, Barkhausen wire elements and high-permeability elements. The applied field which causes switching depends on the magnitude of the component of the interrogation field vector in the direction of the element Referring to FIG. 2, the tag 1 is attached to an item being labelled or tagged 4, and is placed within an interrogation volume 5 within the interrogation unit 2. The interrogation unit 2 includes an antenna 6, which comprises transmit and receive coil sets 7, 8. The tag 1 is interrogated by a scanning magnetic field 9 generated by the transmit coil set 7 under the control 10 of the processor/controller 3. In response to the interrogating magnetic field 9, the tag 1 generates a detectable magnetic field response 11, which is detected by the receive coil set 8. The processor/controller 3 receives input signals 12, 13 from the transmit and receive coil sets 7, 8 respectively and processes the signals to decode data stored on the tag, which is made available at an output 14.

Figure 3:
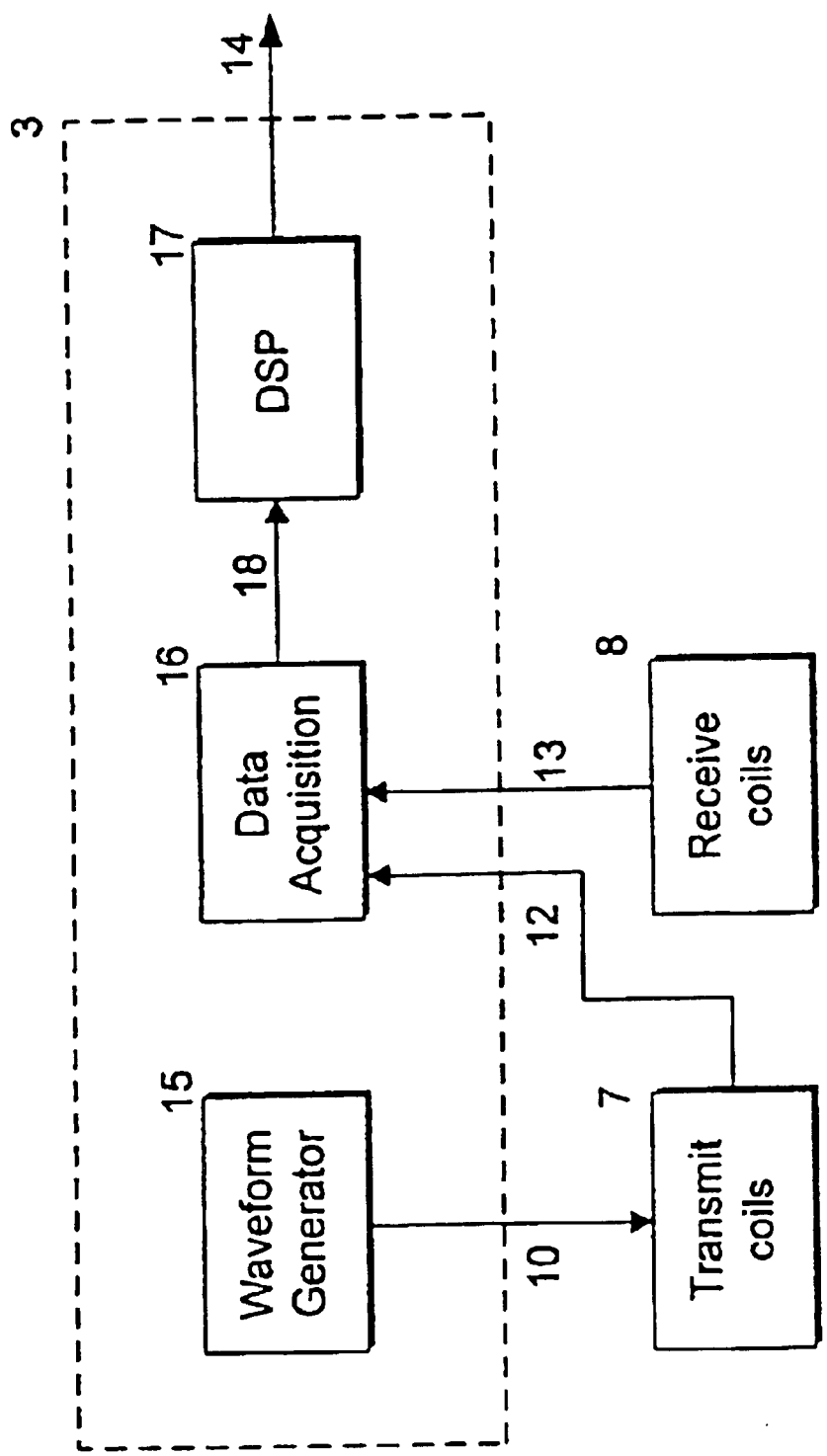
FIG. 3 is a schematic diagram showing details of the signal processor/controller illustrated in FIGS. 1 and 2.

Referring to FIG. 3, the processor/controller 3 comprises a waveform generator for driving the transmit coil set 7, data acquisition circuitry 16 for receiving respective input signals 12, 13 from the transmit and receive coil sets 7, 8 and a digital signal processor 17 for processing the resulting output signals 18 from the data acquisition circuitry 16 to provide the decoded tag data 14.

The transmit and receive coil set arrangement 7, 8 is described in detail by reference to FIGS. 4 to 8.

Figure 4:
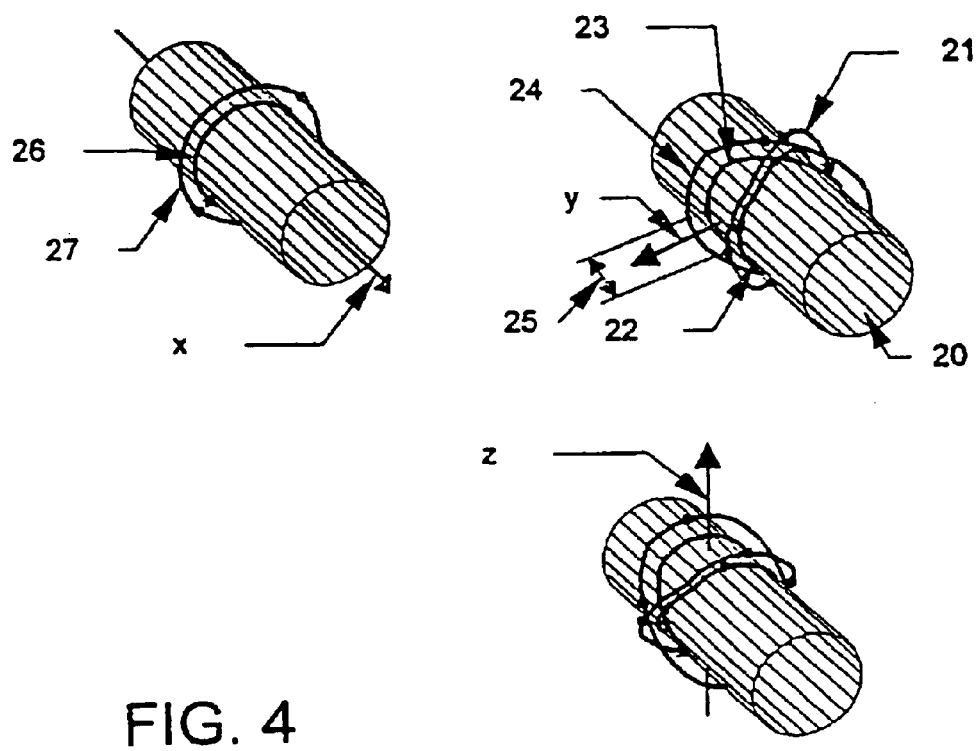
FIGS. 4 and 5 illustrate the receive coil set.
Figure 5:
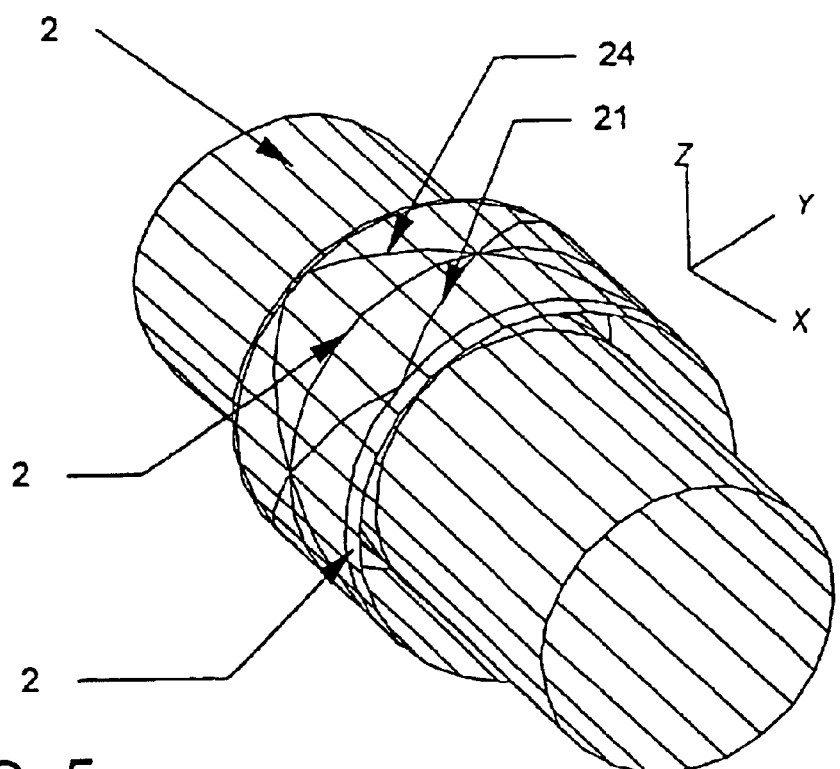

FIGS. 4 and 5 illustrate the receive coil set 8. The receiver coils are constructed on a cylindrical former 20 of diameter 200 mm and length 400mm. FIG. 4 illustrates the three sets of orthogonal coils used to couple with the tag magnetic elements within the interrogation zone. For the y-direction, the receiver coil set comprises 4 coils 21, 22,23, 24. Inner coils 22, 23 lie on the former 20 and extend 120mm along the x-direction 25. Both inner coils 22, 23 comprise 100 turns 0.4 mm ecw. The outer coils 21,24 comprise 58 turns of 0.4 mm ecw and are wound on a second co-axial former (not shown) 260 mm in diameter. The coils extend 156 mm along the x-direction. The four coils 21, 22, 23, 24 are connected in series in the electrical sense illustrated and 'balanced' by small mechanical re-alignments to achieve zero sensitivity to a uniform magnetic field. A second receiver coil set as illustrated is sensitive to tag generated field in the z-direction. This coil set is identical to the coils 21, 22, 23, 24 but rotated through 90° as shown. The third coil set sensitive to tag generated field in the x-direction comprises two solenoid coils 26, 27. The inner coil 26 comprises 100 turns 0.4 mm ecw wound on the former 20, and is 120 mm long. The outer coil 27 comprises 58 turns of 0.4 mm ecw wound on the second 260 mm diameter co-axial former and is 156 mm long. FIG. 5 illustrates all the coils wound on the inner former 20, and the outer former 28.

Figure 6:
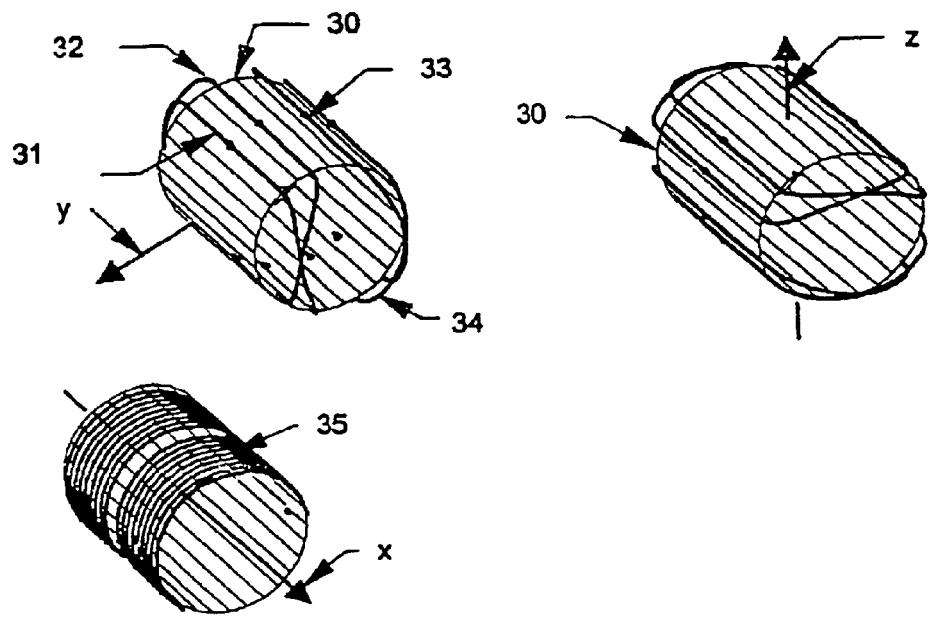
FIGS. 6 and 7 illustrate the transmit coil set.

FIG. 6 illustrates the three orthogonal transmit coils configuration 7. The coils are wound on a cylindrical former 30, 370 mm long and 300 mm diameter. A uniform magnetic field in the y-direction is produced by four coils 31, 32, 33, 34. First and third coils 31, 33 comprise a 'modified Helmholz' arrangement similar to coils 15 and 16. Second and fourth coils 32, 34 comprise a second modified 'Helmholz' arrangement, with a magnetic axis 25° offset from the first and third coils 31, 33. The two 'modified Helmholz' coil sets have magnetic axes 12.5° either side of the y-direction. The first coil 31 comprises 50 turns 1.4 mm ecw and extends 370 mm in length along the former. Where this coil 31 connects across the open end of the former 30, the coil is a flattened half circle with the total coil aperture width of 570 mm. The two edges of the coil 31 that lie along the solenoid (x-direction) subtend 120° at the axial centre of the former. Second to fourth coils 32, 33, 34 are identical in size and form. Their orientation around the former 30 is described above. The four coils are connected in series in the sense illustrated. A second transmit coil set generates uniform field in the z-direction. This set comprises four identical coils orientated in an orthogonal direction as illustrated. The final transmitter coil consists of a long solenoid coil 35 comprising 260 turns of 1.4 mm ecw on the coil former. This generates uniform field in the x-direction.

Figure 7:
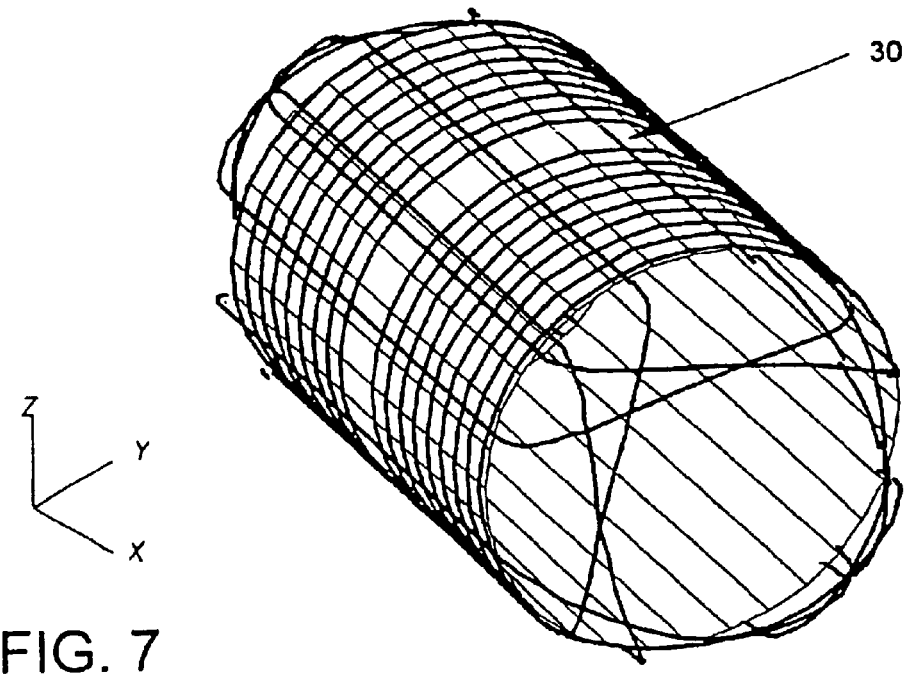
Figure 8:
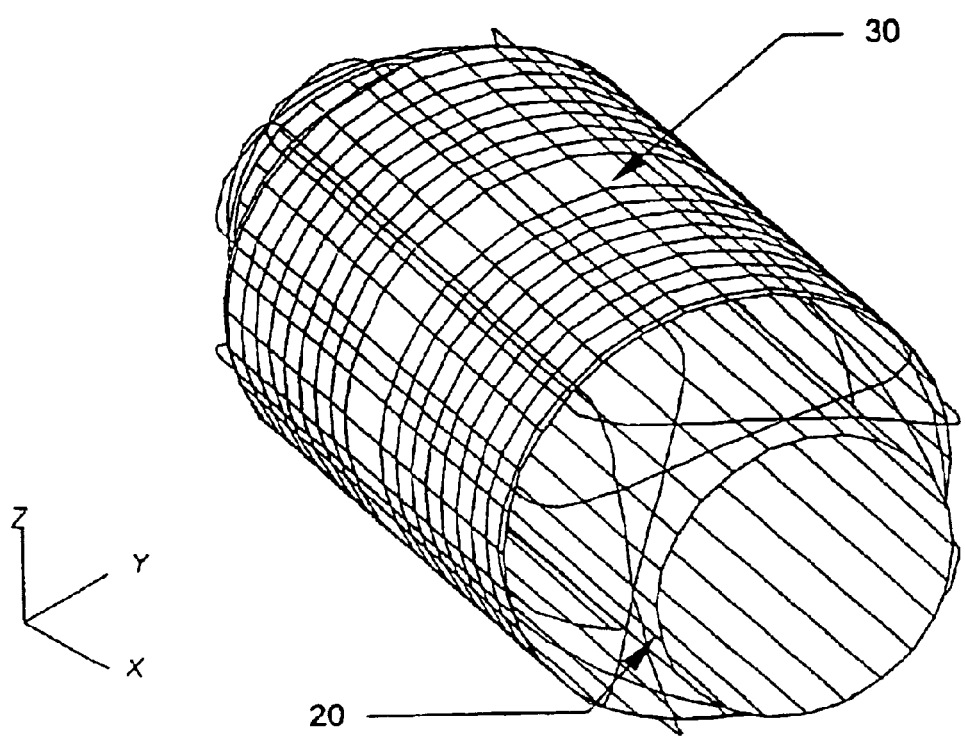
FIG. 8 illustrates the antenna comprising transmit and receive coil sets.

FIG. 7 shows the overall transmit coil arrangement for generating uniform field in three orthogonal directions. FIG. 8 illustrates the antenna 6. The transmit coils on the former 30 are located co-axially with the receiver coil tube 20. The interrogation volume 5 is defined by a further 190 mm ID co-axial tube (not shown) that is used to define a mechanical constraint on possible tag positioning in the antenna 6. The longitudinal region of highest sensitivity is less than 10 cm long and tags can be accurately read when separated by 10 cm or more along the axis of the reader tube.

Figure 9:
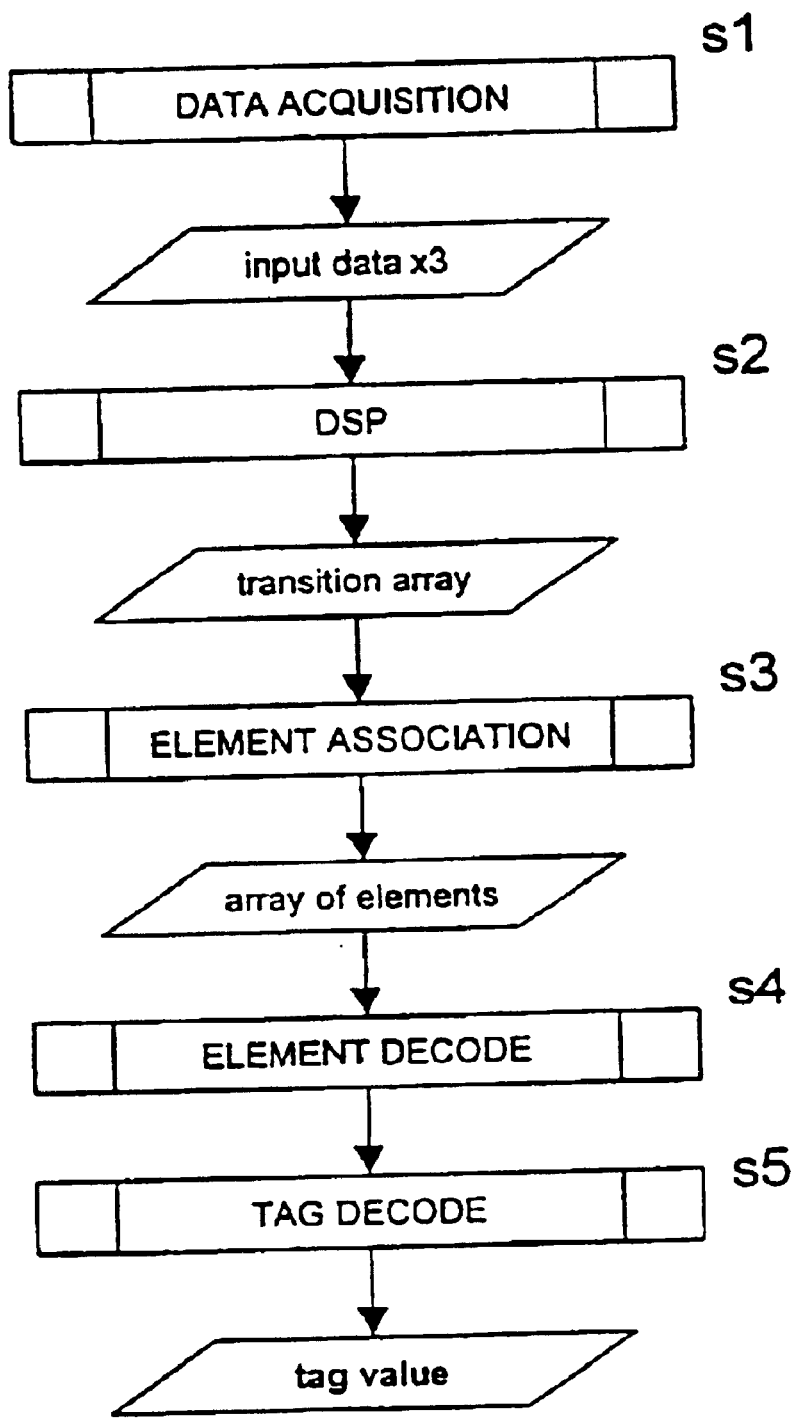
FIG. 9 is a flow chart illustrating the overall processing algorithm.

FIG. 9 illustrates the overall sequence of steps required to decode data stored on a magnetic tag. The first stage is data acquisition (step s1). Data is acquired by detecting the field 11 resulting from the application of a scanning interrogation field 9 to the tag 1, digitising the resulting signals and storing them for subsequent processing. This results in 3 channels of input data, one for each of the x, y and z directions. Digital signal processing is carried out to identify individual switching points, also referred to herein as transitions (step s2). This results in an array of transition information. Each transition is associated with an element (step s3) to provide an array of elements. The elements are then individually decoded (step s4). Finally, the tag is decoded to provide tag value data (step s5).

Data Acquisition

Figure 10:
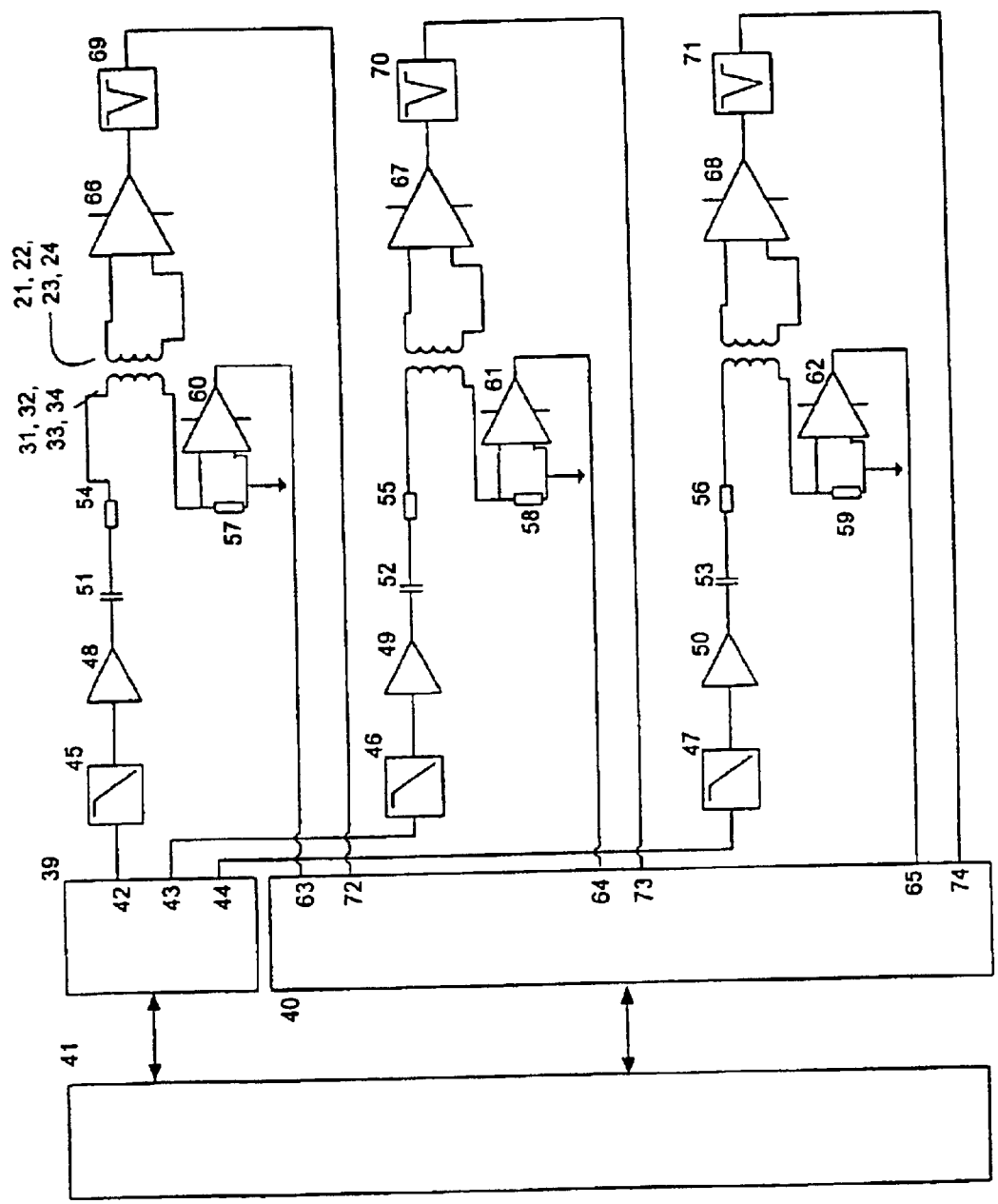
FIG. 10 is a schematic diagram of data acquisition circuitry.

Referring to FIG. 10, an example of the signal processor/controller 3 according to the invention comprises a National Instruments PCI6711 4-channel DAC card 39 for waveform generation and a National Instruments PCI6110E 4-channel ADC card 40 for data acquisition. The cards are mounted into an industry standard IBM compatible PC 41 running Windows 95™. The waveform generation card 39, under software control, generates three transmit excitation voltages 42, 43, 44 which are passed through respective low-pass filters 45, 46, 47 and amplified by respective power amplifiers 48, 49, 50 to drive respective orthogonal transmit coils, which are arranged in a series resonant configuration with respective capacitors 51, 52, 53 and resistors 54, 55, 56. The drive current is for example 3A rms to generate a 2.5 kA/m interrogation field The transmitter currents are monitored by respective current sense resistors 57, 58, 59 which are fed through respective amplifiers 60, 61, 62 as inputs 63, 64, 65 to the data acquisition card 40, where they are digitised at a sample rate of, for example, 160 kH The instantaneous transmit field vector can be determined from these three signals with knowledge of the relationship between the transmit coil field and the current response. For example, pre-calibration of the system is carried out by measuring the transmit field for different values of driving current.

Signals induced in the orthogonal receive coils are amplified by respective amplifiers 66, 67, 68, filtered by respective 130 Hz notch filters 69, 70, 71 to remove any transmit field component, and fed as inputs 72, 73, 74 to the data acquisition card, where they are digitised at a sample rate of, for example, 160 kHz. The data acquisition is buffered in such a fashion that data is clocked into a buffer, and read from the buffer asynchronously at some later point. The buffer depth is sufficient to accommodate the worse-case latency in the subsequent processing step.

A continuous scan is used in this example to interrogate the tag, based on a nominal 130 Hz rotating magnetic field, whose normal vector is arranged to trace out a spiral scan over the surface of a complete sphere, tracing a path from one pole of the sphere to the other and back. The equations for the components of the 'transmitted' B interrogation field are given by:

$$B_x = (\cos^2(\phi)*\cos(\theta) + \sin^2(\phi))*\cos(\omega t) + (\sin(\phi)*\cos(\phi)*\cos(\theta) - \cos(\phi)*\sin(\phi))*\sin(\omega t)$$

$$B_y = (\cos(\phi)*\sin(\phi)*\cos(\theta) - \sin(\phi)*\cos(\phi))*\cos(\omega t) + (\sin^2(\phi)*\cos(\theta) + \cos^2(\phi))*\sin(\omega t)$$

$$B_z = (-\cos(\phi))*\sin(\theta)*\cos((\omega t) - \sin(\theta)*\sin(\phi)*\sin(\omega t)$$

where t is the time, ω is the angular frequency of the 130 Hz scan, $\phi = (\text{constant})* \theta$, and $\theta = \cos t^{-1}(1-t/T)$. T is the total time for one complete interrogation.

Figure 11:
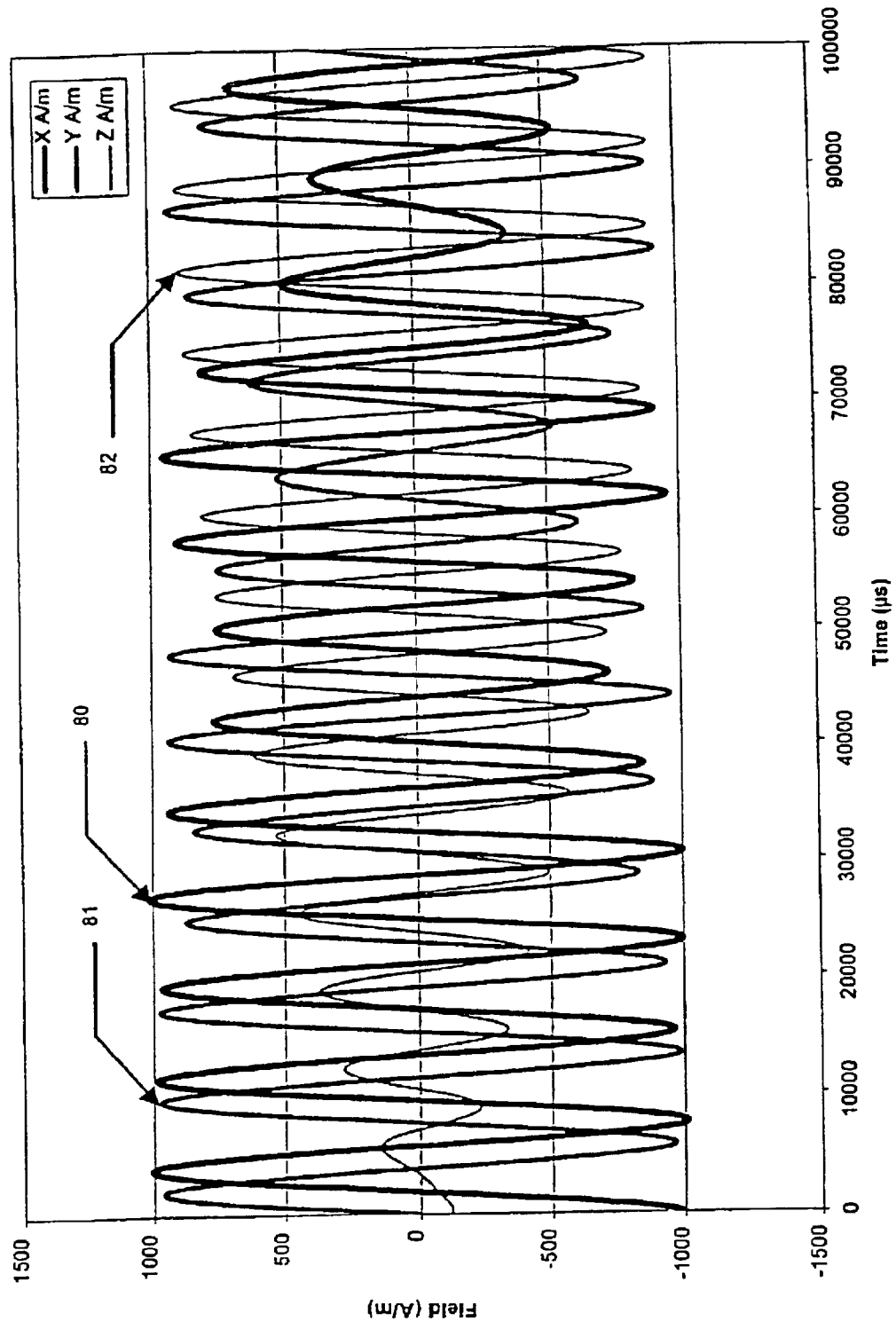
FIG. 11 illustrates the transmit current waveforms.

FIG. 11 shows the three transmit current waveforms 80, 81, 82 received at the inputs 63, 64, 65 of the data acquisition card 40.

Digital Signal Processing

The digital signal processing stage (step s2) performed on the data input to the data acquisition card 40 is now described with reference to the flow chart description of the processing algorithms in FIG. 12.

The purpose of the DSP algorithm is to identify individual transitions, and to record all the relevant parameters on each transition for subsequent processing algorithms. This leads to a large reduction in the volume of data passed on to the subsequent processing stages.

Figure 13:
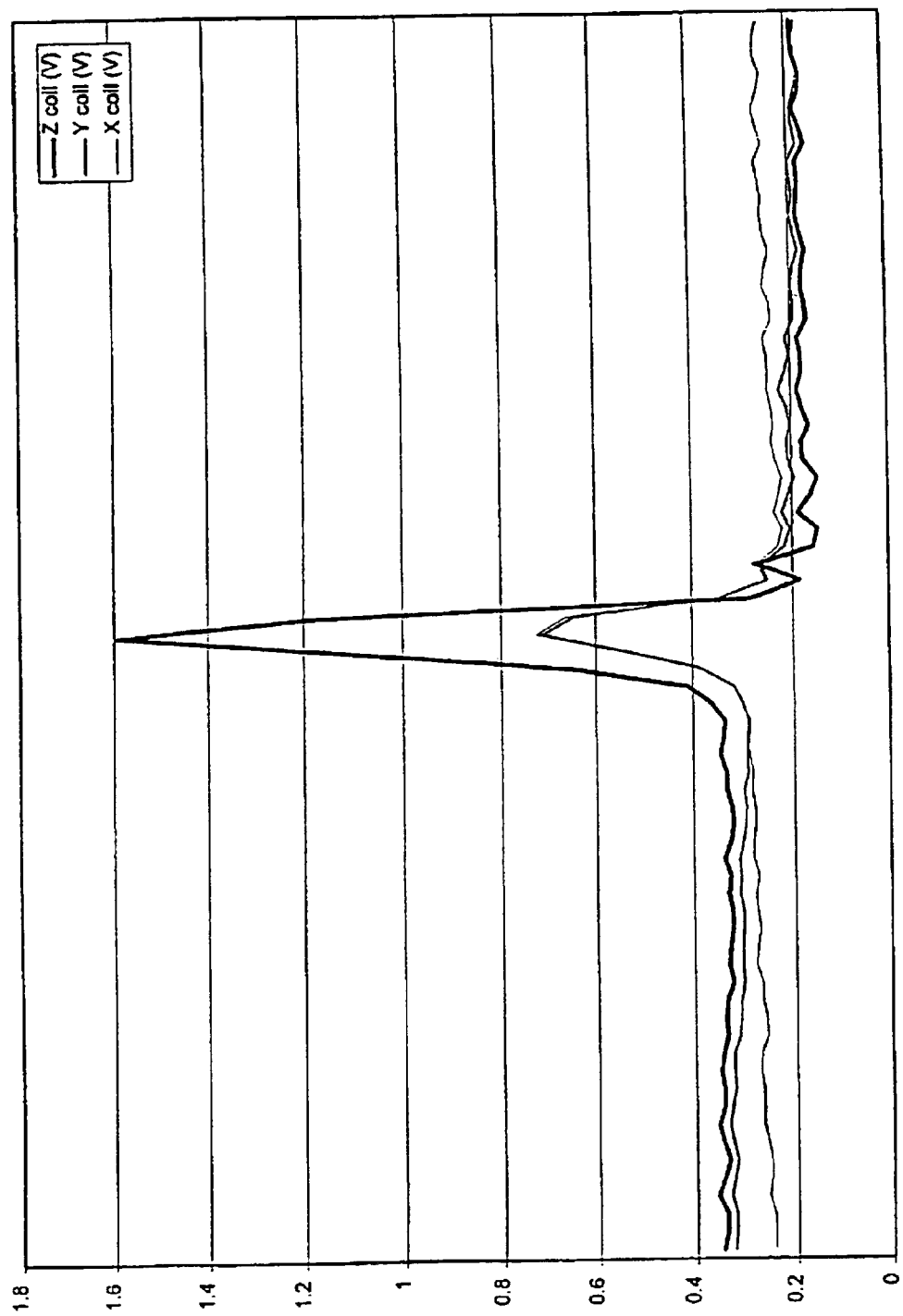
FIG. 13 illustrates signals at the inputs to the ADC from the x, y and z receiver coil preamplifiers, for a single element transition.

The DSP algorithm operates on the three channels of sample data produced by the, data acquisition process. FIG. 13 shows the raw impulse responses in the x, y and z channels for a single transition.

Figure 12:
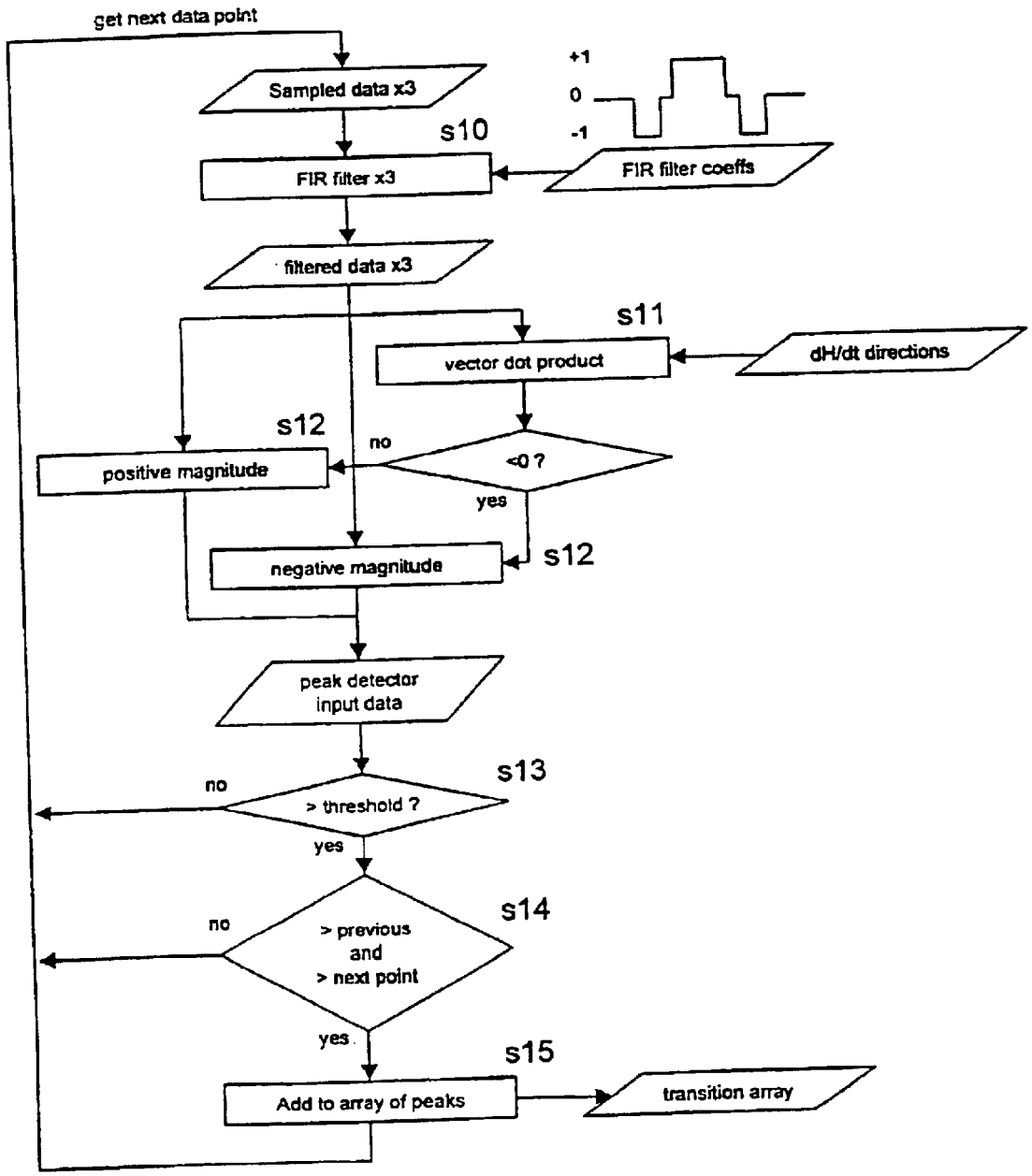
FIG. 12 illustrates a flow chart for the signal processing and filtering algorithm.

Referring to FIG. 12, in a first step s10, an FIR filter is applied to all three channels to produce three sets of filtered data, which form a receiver vector. The simplest filter consists of three rectangular sections, and provides a method of measuring the height of the peaks in the raw data. If the central section has width w and height+1, then the outer two sections have width w/2 and height−1. The width, w, is typically the same value as the response time of the magnetic element, for example, 20–30μs.

Figure 14:
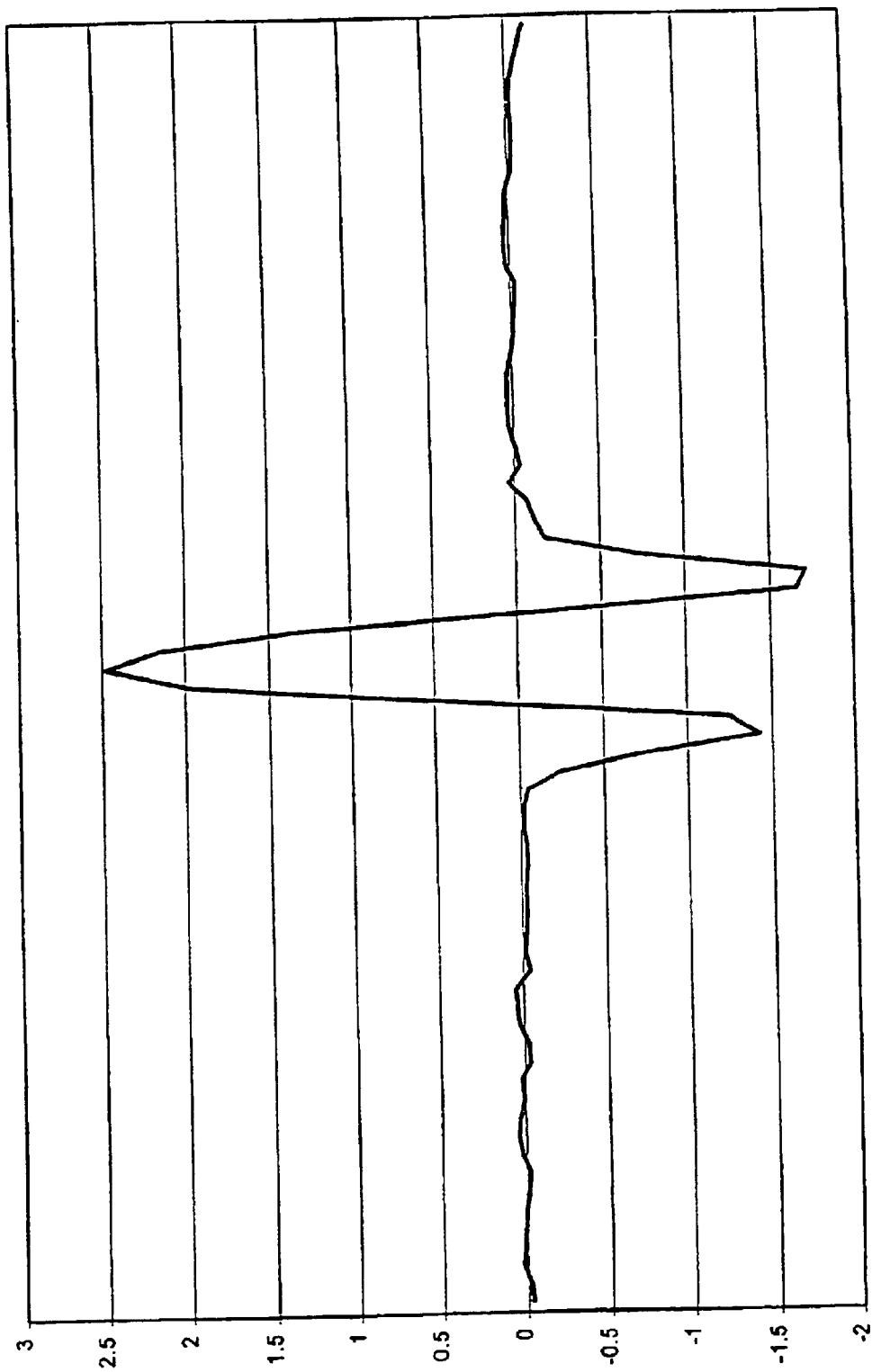
FIG. 14 illustrates the composite filter output of the signal in FIG. 13.

The transmit field vector, H, is used to determine the correct polarity of the element transition in each of the x, y and z receiver coils. The transition polarity in any receiver coil is directly related to the polarity of the rate of change of the field vector dH/dt in the direction of the receiver coil.

dH/dt values are used to produce a "polarity vector", where each component can take the value±1. The scalar (dot) product of the polarity vector with the filtered receiver vector is calculated (step s11) and the receiver vector magnitude, a positive number, is multiplied by the sign (±1) of the result (step s12). This results in the composite signal shown in FIG. 14, in which the polarity of transitions for every element is always the same, allowing the use of a simple peak detector to determine peak values.

Peak detection techniques are well known in the art. In this case, a simple threshold is used to gate the peak detector input data, to avoid noise appearing as spurious peaks. A peak is identified when three or more values exceed the threshold (step s13), and where the current value is greater than both the previous and next value (step s14) The time of the peak is interpolated to a greater resolution than the sample frequency by a simple quadratic fit to these three points.

The data for each transition is stored in an array (step s15). The data includes:

Time

Field vector (H)

Rate of change of field vector (dH/dt)

Receiver vectors (both raw and FIR filtered)

Element Association

The function of the element association algorithm is to associate transition data points with particular magnetic elements in the tag. Subsequent processing steps can then analyse the data for each magnetic element in isolation, thereby reducing an apparently complex problem with multiple elements into a series of relatively simple numerical solves.

There are two primary mechanisms that are used to associate transitions with elements, depending on whether the elements are generally parallel or not. These are described below. In the general case, the first step is to separate into groups using a non-parallel algorithm, and then, if required, to analyse each separate group to see if it contains more than one parallel or near-parallel elements.

Figure 15:
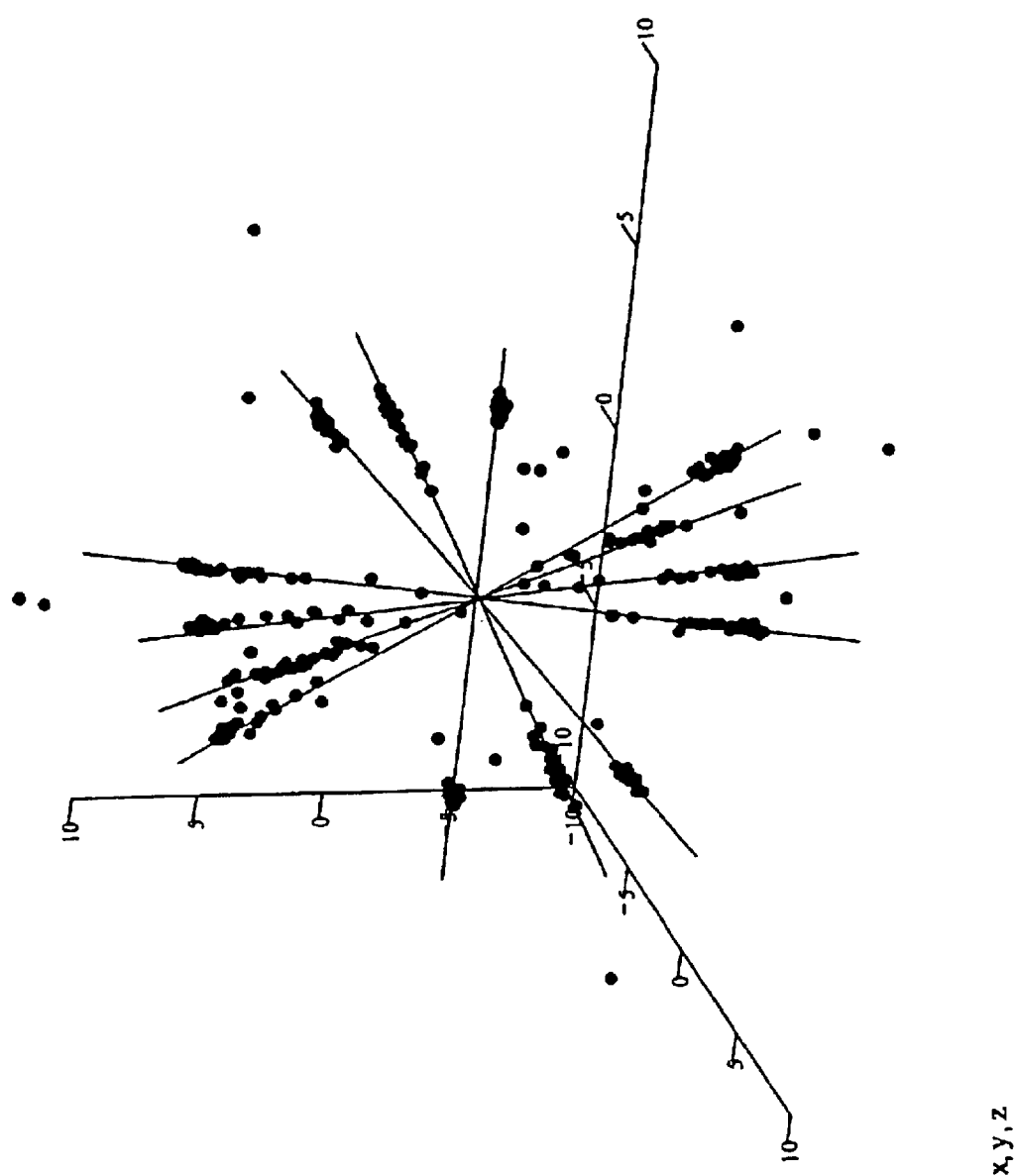
FIG. 15 illustrates a 3D scatter plot of the filtered receiver vectors.

For non-parallel elements, the filtered receiver vectors are used to separate out the transitions between elements. This can be clearly seen from FIG. 15, which shows the filtered receiver vectors in a 3D scatter plot for an example tag having seven non-parallel elements. Inspection of the plot shows that the majority of the transition points Hie along one of 7 different lines through the origin, which indicates that there are 7 discernible directions of elements in the example tag. Each direction can be described by two parameters, and therefore the transitions can be clustered together into groups in 2D. There are a number of different appropriate techniques than can be used to achieve this multi-dimensional clustering (e.g. S. Makeig, S. Enghoff, T -P. Jung, M. Westerfield, J. Townsend, E. Courchesne and T. J. Sejnowski, "Moving-Window. Independent Component Analysis of Event-Related EEG Data: Component Stability, Journal of Neurophysiology"). Additional knowledge about the particular tag construction can be useful to simplify the problem. For example, if all the elements are in the same plane, then the problem can be reduced to a one-dimensional problem Knowledge of the number of elements expected can assist in the clustering process.

Figure 16:
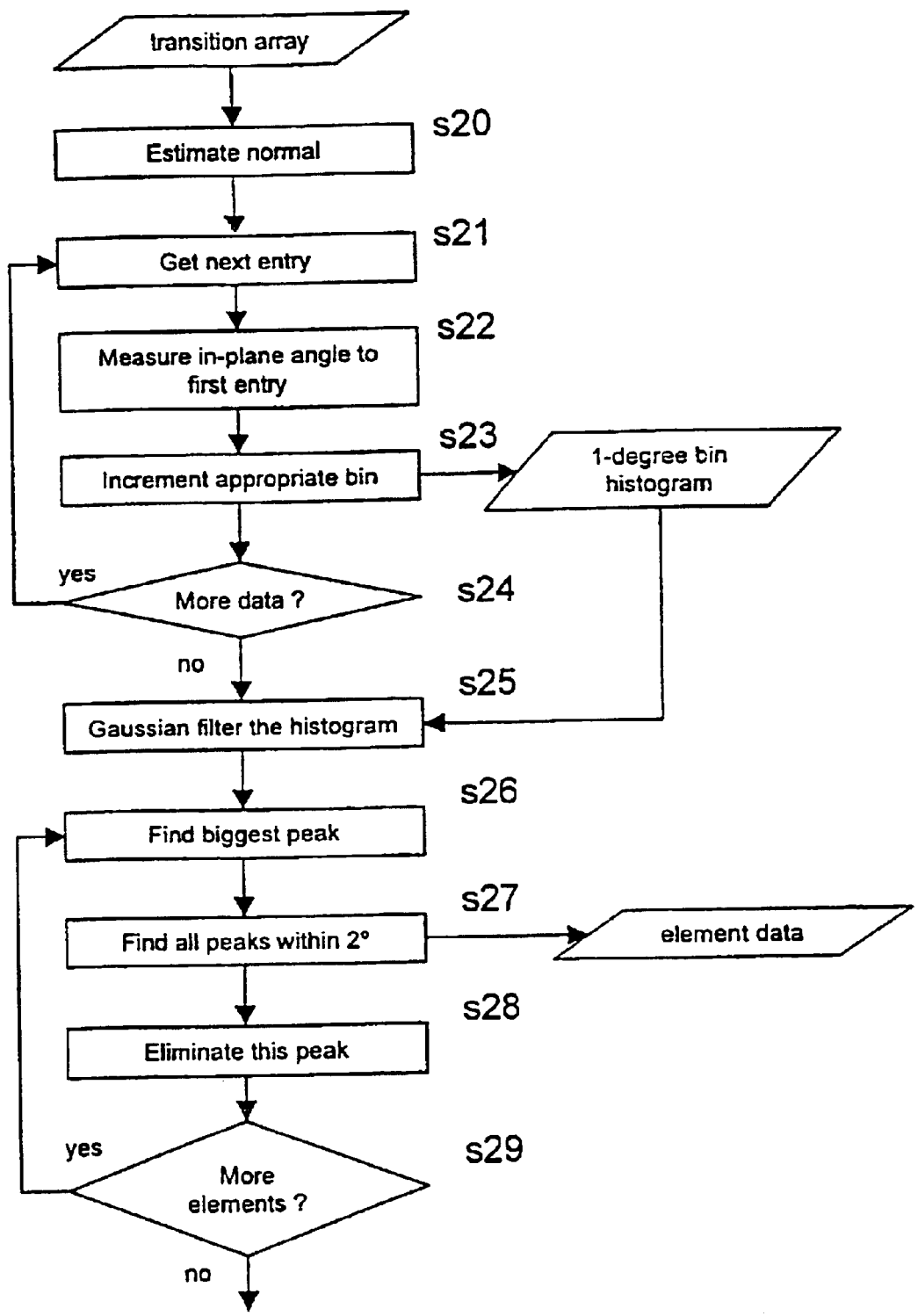
FIG. 16 illustrates a flowchart for the clustering algorithm used for planar tags.

In the particular case of a planar tag, with a known number of elements, the algorithm outlined in FIG. 16 is used. The normal to the plane of the transitions is determined by, for example, a numerical process (step s20). For example, the dot product of every receiver vector with an estimated direction vector is calculated, and this process is iterated until the sum of the magnitude of the dot products is minimised. This reduces the problem to a 1-D problem i.e. the angle in the plane. An in-plane set of vectors can be calculated from the original set of vectors simply by subtracting from each vector in turn the dot product of itself with the normal to the plane. In-plane angles between any two in-plane vectors can them simply be calculated in the usual way using dot products. All the in-plane angles are wrapped into the range 0–180° by adding or subtracting multiples of 180° as required. The algorithm calculates a histogram of in-plane angles relative to some arbitrary datum, such as the first point. For example, if the histogram bins are 1° wide, then the nth bin will contain a count of the number of angles that fall in the range n° to (n+1)°. This will typically give a series of peaks, one for each element. For example, the algorithm obtains the second point from the transition array (step s21), measures the in-plane angle relative to the first point (step s22) and increments the appropriate bin of the histogram (step s23). This process is repeated until all the data has been processed (step s24). After applying Gaussian smoothing to the histogram data (step s25), the direction of an element in the tag can be found by determining the highest peak in this histogram (step s26). To determine the transitions that belong to the element in a given direction, the algorithm finds all the transitions that are within, say, 2° (in plane) of this direction (step s27). The processed peak is then eliminated from the calculation (step s28) and this processing sequence is repeated (steps s26 to s28) until all the data has been processed (step s29).

To separate parallel elements, the algorithm makes use of two properties of a continuous scan of the field vector, H, around the elements, first that the elements transition in order from the lowest to the highest coercivity and second, that the field vector, H, rotates by at least 90° between the last transition of the highest coercivity element in one direction and the first transition of the lowest coercivity element in the reverse direction.

Figure 17:
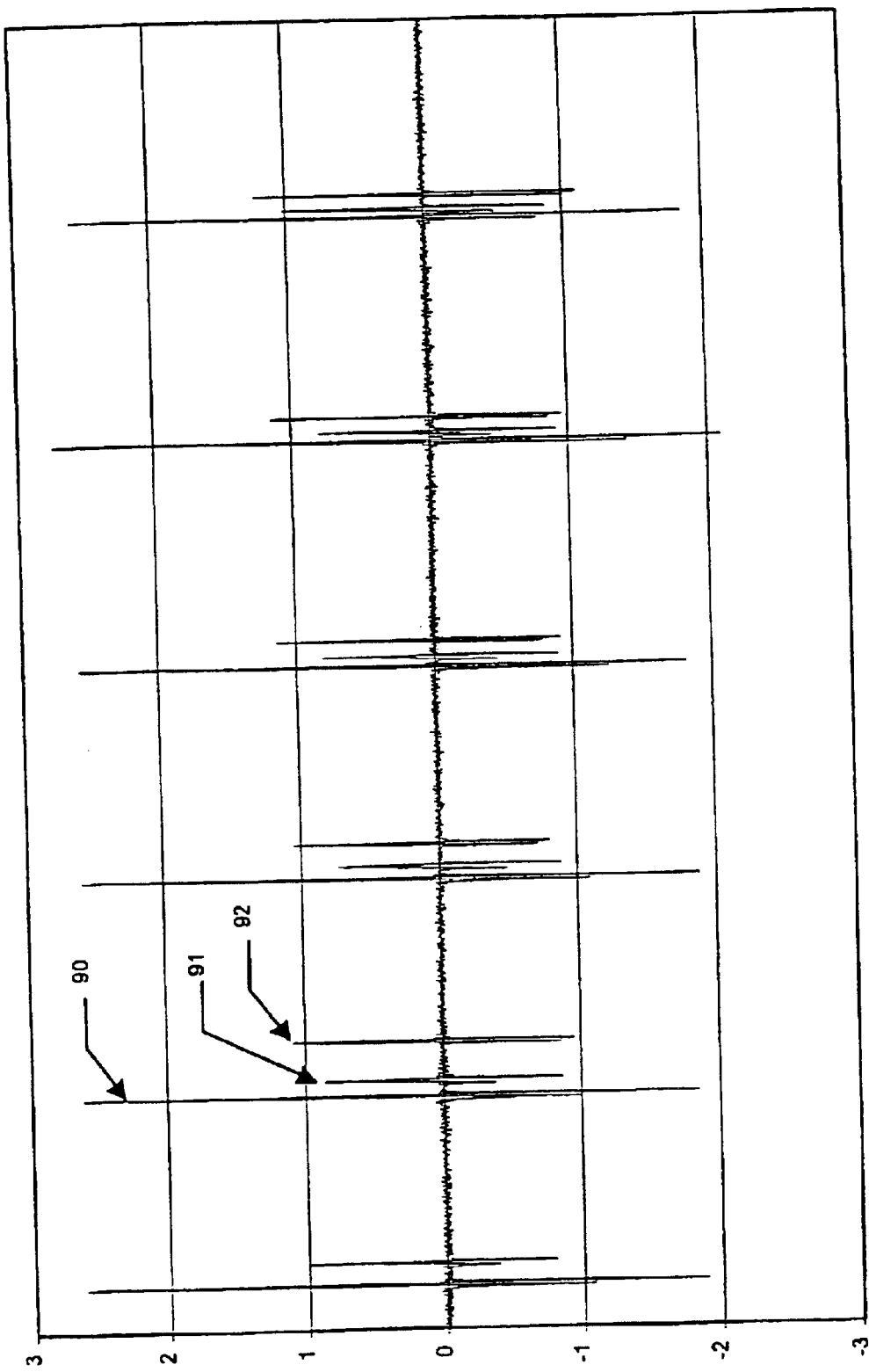
FIG. 17 illustrates the composite filter output for three parallel elements.
Figure 18:
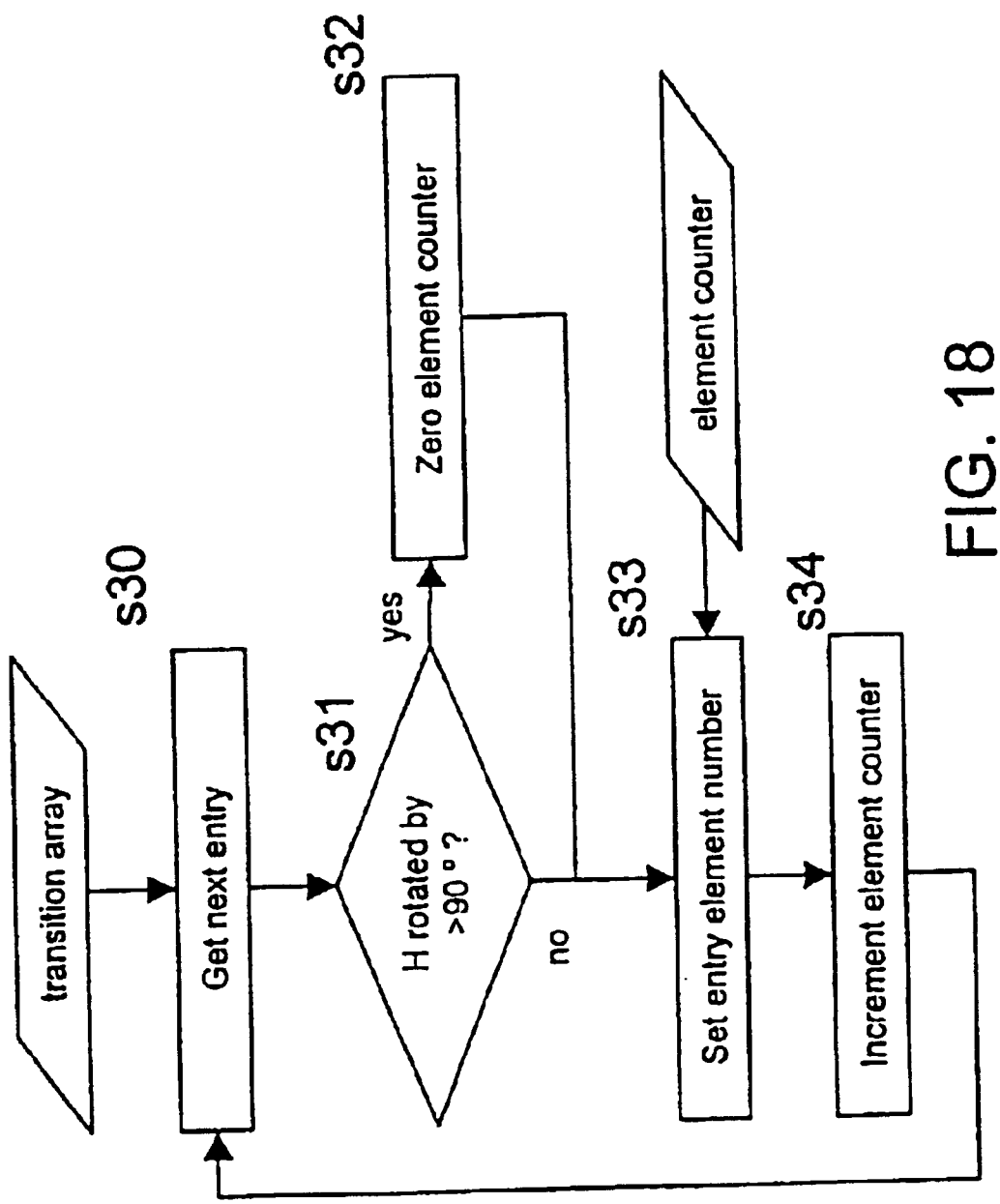
FIG. 18 illustrates a flowchart for a parallel element clustering algorithm.

If some of the elements do not change state, because the transmit field does not reach a high enough value, then there will be fewer transitions, in a 180° scan, than there are elements. In this case, transitions are "lost", starting with the highest-coercivity element. FIG. 17 shows the filtered composite waveform over a few rotations of transmit field, for three parallel elements with different coercivities. Each element is associated with a respective peak 90, 91, 92 and it is relatively straightforward to separate out the transitions belonging to different elements. An outline algorithm to achieve this is shown in FIG. 18.

This works by maintaining an element counter that is incremented each time a new transition is identified, and set to zero each time the field rotates by more than 90° between transitions. Data is extracted from the transition array (step s30) and the algorithm determines whether the transmit field has rotated by more than 90° since the last transition point (step s31). If it has, the element counter is reset to zero (step s32). Following this, the element number corresponding to the transition is set according to the current value of the element counter (step s33). The element counter is then incremented (step s34) and the process repeated for the next transition point (step s30). For example, the first transition following the zeroing of the element counter is associated with element 0, the next with element 1 and so on, until the field has rotated by more than 90 degrees.

Element Decode

The purpose of the element decoding algorithm is to take transition data belonging to one element, and to determine the best-fit direction vector for this element. Once the direction is known, the coercivity of the element, and any net DC field or "bias" along the element vector can be calculated.

Figure 19:
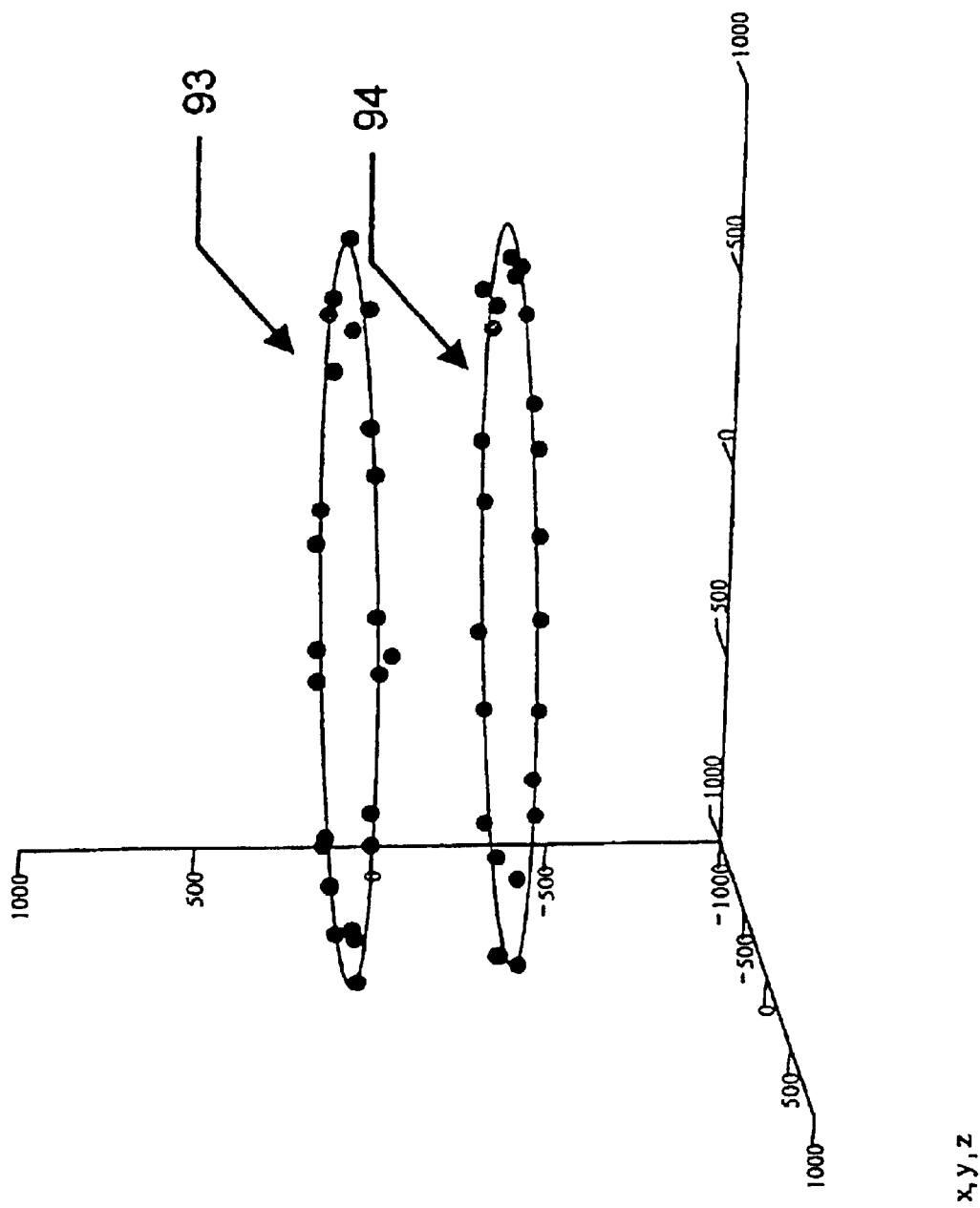
FIG. 19 illustrates a 3D scatter plot of the transition field vectors for a single element.
Figure 20:
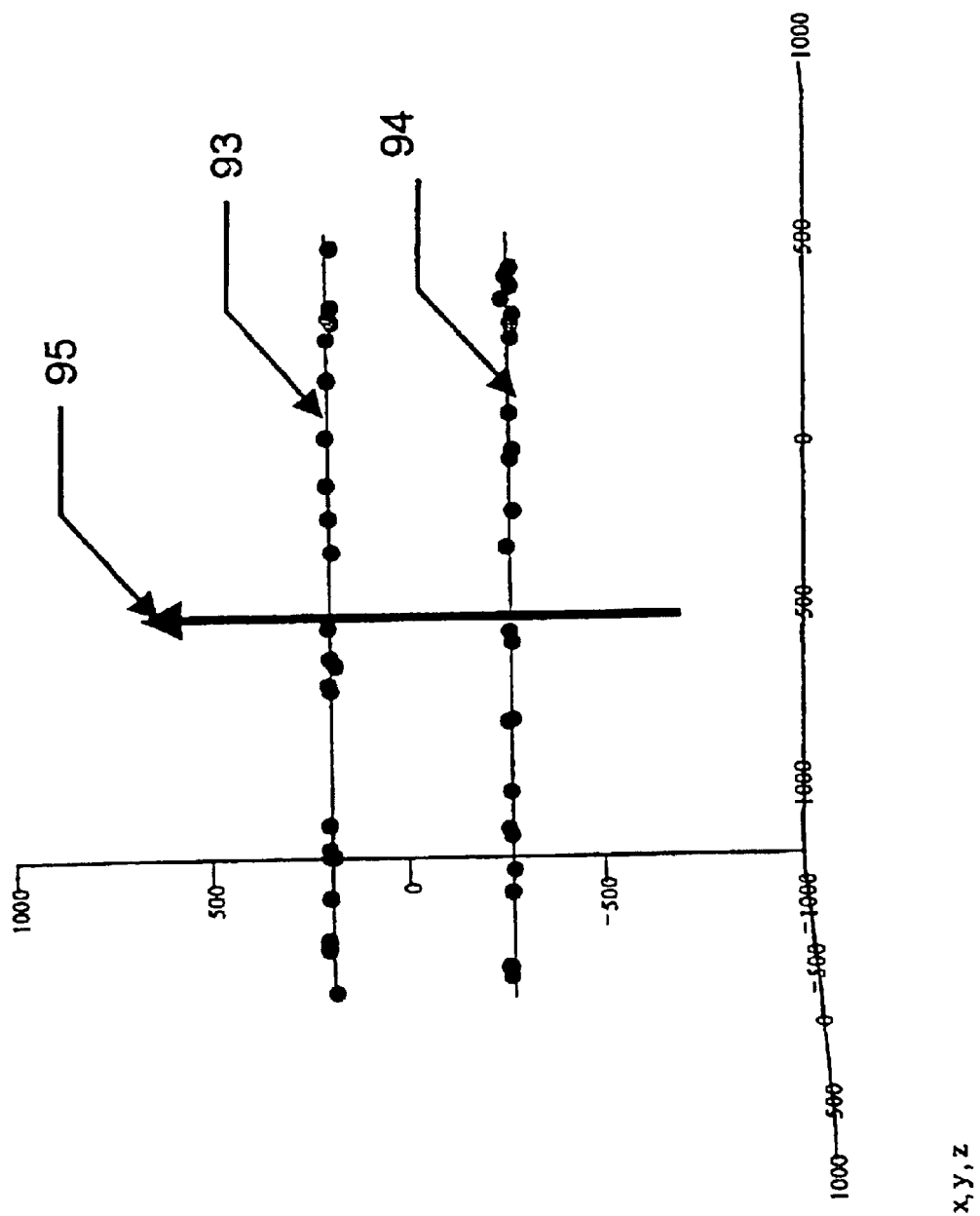

FIG. 19 is a 3D scatter plot of transition point field vectors, for a single bistable magnetic element with a finite coercivity. In this example, the field has been scanned approximately over the surface of a sphere, so the transition points lie roughly on two circles 93, 94. More generally, the transition points would be expected to lie on one of two planes. By tilting the view of the transition data in the scatter plot, it is possible to show the two planes edge-on, as illustrated in FIG. 20. The bold vertical arrow 95 shows the element vector.

Figure 21:
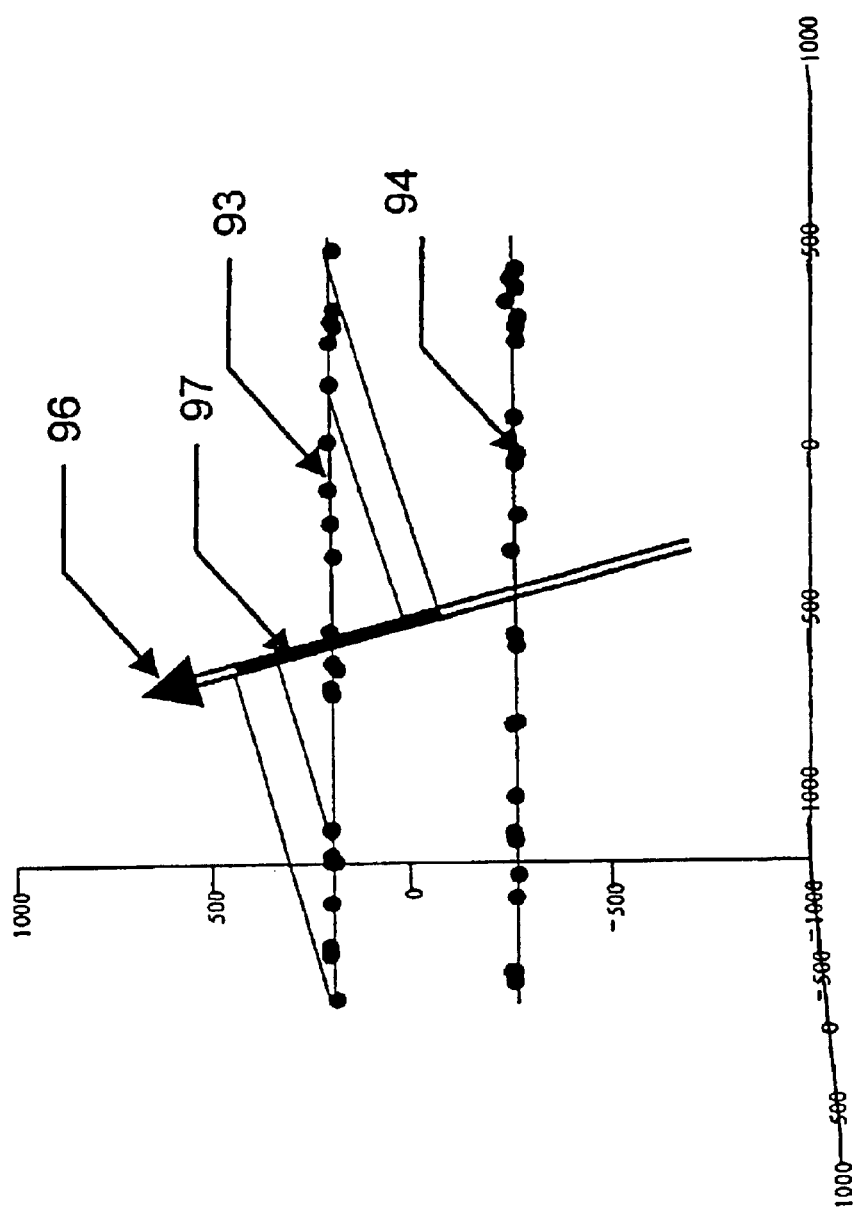
FIG. 21 illustrates distribution of field vectors that occur along a misaligned element direction vector.

The element decoding algorithm attempts to determine the best vector direction for the element, by minimising the scatter of field vectors resolved in this direction. FIG. 21 illustrates the situation where a guess 96 has been taken for the element vector that is not in the correct direction. Taking the upper set of transitions 93, it is clear that when these are projected onto the element vector 96, they form an extended distribution 97 (shown by a darkened section) along the vector 96. As the vector is rotated around, the extent of this distribution will be smallest when the vector is closest to the actual direction of the tag element.

Figure 22:
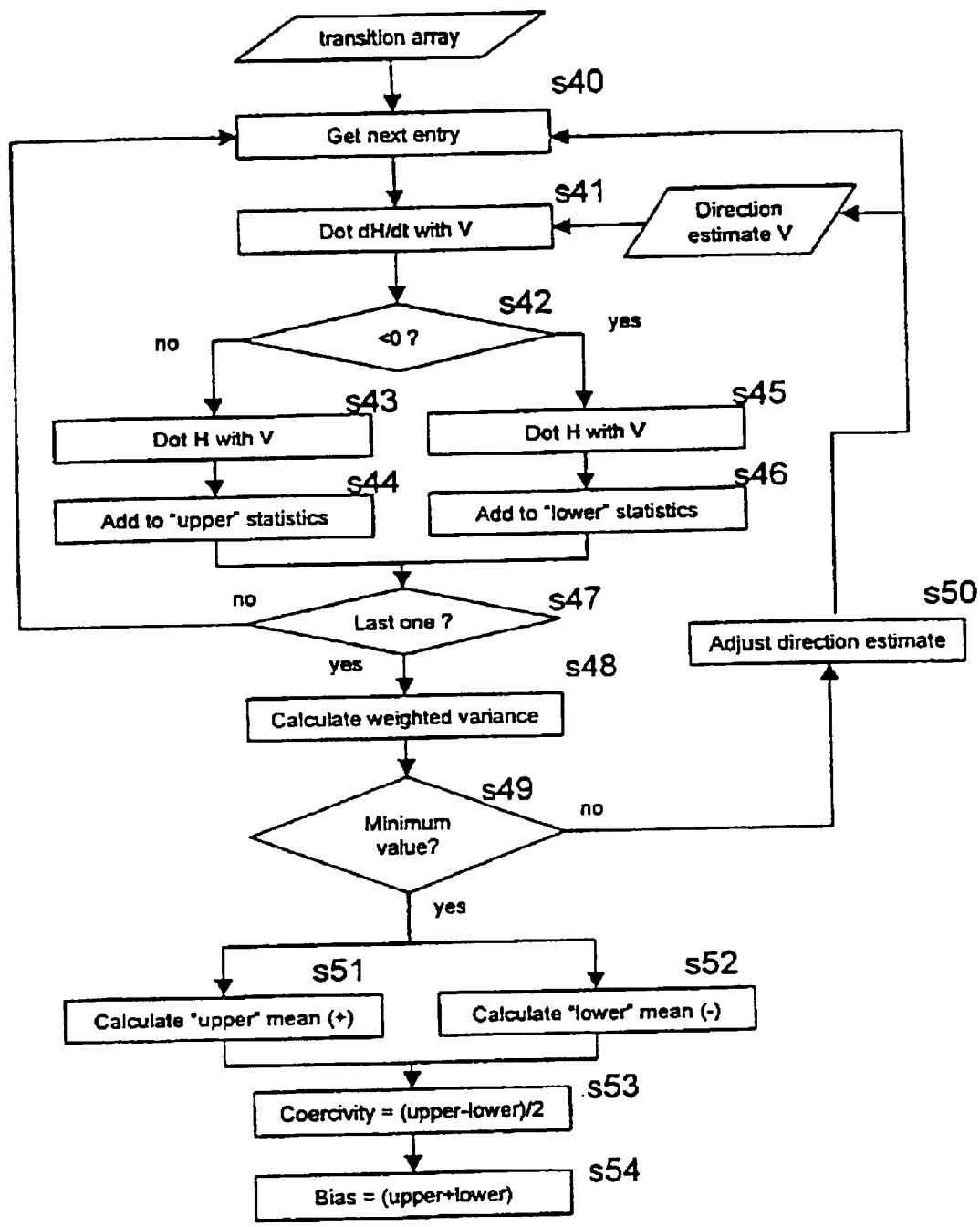
FIG. 22 illustrates a flowchart for the calculation of the mean switching field, switching field variance, coercivity and DC bias field.

FIG. 22 shows a flowchart for the algorithm used to calculate the error used in the iterative solving process. The algorithm uses the current guess for the element vector direction, V. Initially, this is the vector direction from the element association algorithm.

The first data point is retrieved (step s40) and the dot product of the direction estimate V with the polarity vector for dH/dt is calculated, as described in relation to FIG. 12 above (step s41). If this is positive (step s42) i.e. for the upper set of transitions, then the dot product of the field vector and the element vector is calculated (step s43) and added to the upper set of statistics (step s44). The dot product resolves the component of the field vector along the element vector. The same calculation is carried out for the lower set of transitions (steps s45, s46), indicated by the negative dot product at step s41. The upper and lower (forward and reverse) sets of transitions are distinguished by the sign of dH/dt along the direction of the element, or alternatively by the sign of the filtered receiver vector along the direction of the element. This procedure is repeated for all the data points (step s47). An average value of variance is calculated from the variances for each of the upper and lower sets of transitions separately, weighted by the number of transitions in the upper and lower sets of transitions (step s48). A standard formula is used to calculate the variance for each set of data. For a set of measured data points, x, the variance, var(x) is the mean of the squares of x minus the square of the mean of x, or mathematically $$var(x) = \langle x^2 \rangle - \langle x \rangle^2$$

The weighted variance of $N_w$ upper transition points, u, with variance var(u) and $N_l$ lower transition points, l, with variance var(l) is then given by:

$$var = \frac{N_u var(u) + N_l var(l)}{N_u + N_l}$$

The weighted variance is used as a measure of the error in the guessed vector direction. When the guessed direction is equal to the actual element direction, the weighted variance will generally have its minimum value. The value will never fall to zero, because there is always a certain amount of noise in the determination of the transition field, arising from sources such as electronic noise and randomness in the material behaviour. In the simplest case, the variance is a function (numerically evaluated, rather than an analytic function) of two direction variables, such as θ and φ from the spherical polar co-ordinates (r, θ, φ). The value of this function can be minimised using a standard numerical minimisation algorithm. The variance varies approximately quadratically with the deviation from the ideal direction, and this means that the minimisation algorithm can be extremely efficient (the "quadratic" case is generally considered to be the easiest). Multi-variate numerical minimisation algorithms are well known in the art—for example, Powell's method When the weighted variance is not minimum (step s49), the direction estimate V is adjusted in accordance with the appropriate minimisation algorithm (step s50) and the algorithm re-run with the new value of V. When the weighted variance is minimised, the mean values of the field for the upper and lower sets of transitions are calculated (steps s51, s52). The coercivity of the element is calculated as half the difference between the two switching fields (step s53), while the DC field along the element is calculated as the sum of the two switching fields (step s54).

Additional parameters as well as direction can usefully be added to the numerical minimisation. The most important term to add is the vector velocity, which allows the algorithm to deal with the movement of the tag elements during the decoding process. The element direction in steps s41, s43, s45 is then a function of the time at which the transition occurs, and the function for the variance then depends on four parameters (for example θ, φ, dθ/dt and dφ/dt). Once again, this function can simply be minimised using a standard multi-variate minimisation algorithm Many magnetic elements do not behave ideally, and show significant changes in their switching field (or coercivity) depending on the value of dH/dt. A general form for the switching field, $H_{switch}$, resolved along the element is:

$$H_{switch} = H_0 + k_a\left(\frac{dH}{dt}\right)^a + k_b\left(\frac{dH}{dt}\right)^b + \ldots$$

where a,b etc are arbitrary powers. If the coefficients k are known, then the value of $H_0$ can be calculated from the measured switching field, and the variance of this value can be minimised as before. If the coefficients k are not known, but the values a, b are known, then the function for the numerical minimisation can also include the coefficients, k, as function arguments, as well as the direction and velocity terms. In this case, the values of k can be used to distinguish between different types of materials and thereby store more data.

Anisotropic thin-film magnetic materials can exhibit a further form of non-ideal behaviour. For materials with an easy-axis of magnetisation, the in-plane field perpendicular to the easy axis can influence the field at which the material switches. A similar approach to the one described above can be used to calculate a nominally constant value, $H_0$, from the raw switching points.

Tag Decode

The primary output data for each magnetic element from a reader according to the invention is as follows:

Orientation in the reader (vector)
Coercivity of the element (scalar)
Bias field along each element (scalar)
Amplitude response (scalar)
Secondary data for each element includes
dH/dt coefficients
Perpendicular field coefficients
Response time
Characteristic response "shape" or spectrum
Statistical distribution of primary parameters This data assumes little about the construction of the tag. The structure of the tag (e.g. which elements share bias magnet elements) may be used to provide more detail—for example, the magnitude and direction of an overall bias field. The details of the chosen coding scheme are used to translate all these raw parameters into useful data stored on the tag.

The above examples of the invention are intended to be illustrative, rather than restrictive. A person skilled in the art would understand that various modifications and variations in the detailed implementation are possible, and are considered to be within the scope and spirit of the invention as defined in the appended claims.

What is claimed is:

1. A method of reading a magnetic tag having at least one magnetic element, comprising;
   interrogating the tag with a scanning magnetic field;
   determining transition data associated with changes in the magnetisation state of the at least one magnetic element;
   associating the transition data with one or more respective magnetic elements; and
   for each magnetic element, determining the element direction which corresponds to the transition data for that magnetic element.

2. A method according to claim 1, wherein the step of determining the magnetic element direction comprises selecting the direction which minimises the scatter of transition field vectors resolved along the direction of the magnetic element.

3. A method according to claim 1, including grouping the transition data by the type of magnetic element transition.

4. A method according to claim 3, comprising grouping first and second types of magnetic element transition.

5. A method according to claim 4, wherein the first type of magnetic element transition comprises a forward transition and the second type of magnetic element transition comprises a reverse transition.

6. A method according to claim 4, wherein a signal defining a transition is received by one or more receiver coils, including determining the type of transition in accordance with the polarity of the rate of change of the field vector in the direction of the magnetic element.

7. A method according to claim 4, including determining information relating to the switching fields for each of the first and second types of transition.

8. A method according to claim 7, comprising determining magnetic element characteristics from said switching field information relating to transition data associated with a magnetic element.

9. A method according to claim 8, further comprising calculating the coercivity of the magnetic element as substantially half the difference between first and second switching fields.

10. A method according to claim 8, further comprising calculating the bias field on the magnetic element as substantially the sum of first and second switching fields.

11. A method according to claim 9, wherein the first switching field comprises the mean value of the switching fields for the first type of transition and the second switching field comprises the mean value of the switching fields for the second type of transition.

12. A method according to claim 1, including associating the transition data with one or more respective magnetic elements using a receiver vector whose components represent the amplitudes of the signals in one or more receive coils.

13. A method according to claim 1, comprising scanning the tag using a rotating magnetic field.

14. A method according to claim 13, in which the tag comprises a plurality of magnetic elements, further comprising associating transition data with respective magnetic elements in accordance with the order in which the magnetic elements transition in response to the rotating field.

15. A method according to claim 1, comprising determining the coercivity, the local magnetic field bias resolved in the direction of each magnetic element and the orientation of each magnetic element relative to a known interrogation field reference frame.

16. A method according to claim 1, further comprising determining the amplitude response of each magnetic element to the applied magnetic field.

17. A method of distinguishing between a plurality of magnetic elements, comprising the steps of:
  applying a scanning magnetic field to the magnetic elements; determining the direction of each of the magnetic elements;
  for each of the magnetic elements, determining the components of the field in the direction of the magnetic element at which the magnetic element switches magnetisation states; and
  from said components, determining, for each of the magnetic elements, respective characteristics of the magnetic element.

18. A method according to claim 17, comprising determining first and second switching components as the components when the rate of change of the field along the direction of the magnetic element is positive and negative respectively.

19. A method according to claim 17 wherein the respective characteristics comprise the coercivities of the magnetic elements.

20. A method according to claim 17, comprising storing data by reference to the respective characteristics of the magnetic elements.

21. A method according to claim 20, wherein data is storable by reference to any one or more of orientation of the magnetic elements, coercivity, bias field along the magnetic element and amplitude response.

22. A method according to claim 20, wherein data is storable by reference to parameters relating to any one or more of rate of change of applied field, perpendicular field, response time, characteristic response shape and the statistical distribution of the parameters.

23. A method of determining, for a magnetic element, any one or more of a plurality of characteristics comprising the coercivity of the magnetic element, the local magnetic field bias resolved in the direction of the magnetic element and the orientation of the magnetic element, comprising:
  applying a varying magnetic field to the magnetic element;
  determining the direction of the magnetic element;
  determining the components of the field in the direction of the magnetic element at which the magnetic element switches magnetisation states; and
  from said components, determining the one or more characteristics of the magnetic element.

24. A computer program, which when run on a computer, is configured to carry out a method of reading a magnetic tag having at least one magnetic element comprising:
  interrogating the tag with a scanning magnetic field;
  determining transition data associated with changes in the magnetisation state of the at least one magnetic element;
  associating the transition data with one or more respective elements; and
  for each element, determining the element direction which corresponds to the transition data for that element.

25. A magnetic tag reader for reading a magnetic tag having at least one magnetic element, comprising:
  means for interrogating the tag with a scanning magnetic field;
  means for determining transition data associated with changes in the magnetisation state of the at least one magnetic element;
  means for associating the transition data with one or more respective magnetic elements; and
  means for determining, for each magnetic element, the magnetic element direction which corresponds to the transition data for that magnetic element.

26. A tag reader according to claim 25, wherein the scanning field comprises a rotating magnetic field.

27. A tag reader according to claim 25, further comprising means for selecting the magnetic element direction which minimises the scatter of transition point field vectors resolved along the direction of the magnetic element.

28. A tag reader according to claim 25, wherein the transition data includes data defining first and second switching fields at which a magnetic element undergoes first and second transitions.

* * * * *